United States Patent
Ezer

(10) Patent No.: US 10,987,003 B2
(45) Date of Patent: Apr. 27, 2021

(54) METHOD AND SYSTEM FOR CLASSIFYING AN INDIVIDUAL AS HAVING OR NOT HAVING DISPOSITION FOR FORMATION OF CEREBRAL ANEURYSM

(71) Applicant: ANEUSCREEN LTD., Netanya (IL)

(72) Inventor: Haim Ezer, Netanya (IL)

(73) Assignee: ANEUSCREEN LTD., Netanya (IL)

( * ) Notice: Subject to any disclaimer, the term of this patent is extended or adjusted under 35 U.S.C. 154(b) by 204 days.

(21) Appl. No.: 16/305,605

(22) PCT Filed: Jun. 1, 2017

(86) PCT No.: PCT/IL2017/050609
§ 371 (c)(1),
(2) Date: Nov. 29, 2018

(87) PCT Pub. No.: WO2017/208242
PCT Pub. Date: Dec. 7, 2017

(65) Prior Publication Data
US 2020/0085318 A1 Mar. 19, 2020

(30) Foreign Application Priority Data
Jun. 2, 2016 (IL) ........................................ 246009

(51) Int. Cl.
*G16H 50/50* (2018.01)
*A61B 5/055* (2006.01)
(Continued)

(52) U.S. Cl.
CPC ........ *A61B 5/02014* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 8,452,062 B2 * 5/2013 Gogin .................. A61B 6/5217
382/128
8,571,278 B2 * 10/2013 Sonka ...................... G06T 7/11
382/128
(Continued)

FOREIGN PATENT DOCUMENTS

CN 1954340 A 4/2007
CN 101990415 A 3/2011
(Continued)

OTHER PUBLICATIONS

Foutrakis, et al., "Saccular Aneurysm Formation in Curved and Bifurcating Arteries", AJNR Am J Neuroradiol, Aug. 20, 1999, pp. 1309-1317.
(Continued)

*Primary Examiner* — Tahmina N Ansari
(74) *Attorney, Agent, or Firm* — Dorsey & Whitney LLP

(57) ABSTRACT

Methods and systems for controlling aneurysm initiation or formation in an individual are presented; the technique comprises receiving morphological data of an artery being indicative of at least first and second geometrical parameters of the artery along its trajectory; analyzing the data to identify at least one flow-diverting location along the artery satisfying first and second predetermined conditions of the geometrical parameters; classifying the individual as having or not having disposition for future formation of an aneurysm, depending respectively on whether the at least one flow-diverting location is identified or not and generating classification data; and generating prediction data for the individual with regard to future aneurysm formation.

19 Claims, 5 Drawing Sheets

(51) Int. Cl.
| | |
|---|---|
| *G06T 17/00* | (2006.01) |
| *A61B 5/02* | (2006.01) |
| *G16H 50/30* | (2018.01) |
| *G16H 50/20* | (2018.01) |
| *G16H 30/40* | (2018.01) |
| *A61B 5/00* | (2006.01) |
| *A61B 5/107* | (2006.01) |

(52) U.S. Cl.
CPC .......... *A61B 5/1075* (2013.01); *A61B 5/4064* (2013.01); *G06T 17/00* (2013.01); *G16H 30/40* (2018.01); *G16H 50/20* (2018.01); *G16H 50/30* (2018.01); *G16H 50/50* (2018.01); *G06T 2207/30016* (2013.01)

(56) References Cited

U.S. PATENT DOCUMENTS

| | | | |
|---|---|---|---|
| 9,349,178 | B1 | 5/2016 | Itu et al. |
| 2008/0065570 | A1 | 3/2008 | Schultz |
| 2008/0094389 | A1 | 4/2008 | Rouet et al. |
| 2008/0188737 | A1 | 8/2008 | Assmann et al. |
| 2009/0136103 | A1* | 5/2009 | Sonka ................ G06K 9/6224 382/128 |
| 2010/0284587 | A1* | 11/2010 | Malek ................ A61B 5/02014 382/128 |
| 2011/0009718 | A1 | 1/2011 | Gavish |
| 2012/0078602 | A1* | 3/2012 | Pfister ................ A61B 6/507 703/11 |
| 2012/0201446 | A1* | 8/2012 | Yang ................ G06T 7/0012 382/134 |
| 2012/0323547 | A1* | 12/2012 | Baloch ................ G16H 50/50 703/11 |
| 2013/0109982 | A1 | 5/2013 | Sato et al. |
| 2014/0348408 | A1 | 11/2014 | Zhu et al. |
| 2020/0085318 | A1* | 3/2020 | Ezer ................ A61B 5/7275 |

FOREIGN PATENT DOCUMENTS

| | | |
|---|---|---|
| CN | 103002798 A | 3/2013 |
| EP | 2749222 A1 | 7/2014 |
| WO | 9938433 A1 | 8/1999 |
| WO | 0010494 A1 | 3/2000 |
| WO | 2008065570 A1 | 6/2008 |
| WO | 2010121146 A2 | 10/2010 |
| WO | 2011008906 A1 | 1/2011 |
| WO | 2014077360 A1 | 5/2014 |
| WO | 2015121674 A1 | 8/2015 |

OTHER PUBLICATIONS

Hacein-Bey, et al., "Current Imaging Assessment and Treatment of Intracranial Aneurysms", Neuroradiology/Head and Neck Imaging, pp. 32-44, Jan. 2011.

Hoi, et al., "Effects of arterial geometry on aneurysm growth: threedimensional computational fluid dynamics study", J Neurosurg, 101, Oct. 2004, pp. 676-681.

Kayembe, et al., "Cerebral Aneurysms and Variations in the Circle of Willis", Stroke, vol. 15, No 5, 1984, pp. 846-850.

Lauric, et al., "Curvature Effect on Hemodynamic Conditions at the Inner Bend of the Carotid Siphon and its Relation to Aneurysm Formation", J Biomech, 47(12), Sep. 22, 2014, pp. 3018-3027.

Lauric, et al., "High curvature of the internal carotid artery is associatd with the presence of intracranial aneurysms", Journal of Neurointerventional Surgery, vol. 6, No. 10, Dec. 7, 2014, pp. 733-739.

Piccinelli, et al., "A Framework for Geometric Analysis of Vascular Structures: Application to Cerebral Aneurysms", IEEE Transactions on Medical Imaging, vol. 28, No. 8, Aug. 2009, pp. 1141-1155.

Piccinelli, et al., "Geometry of the Internal Carotid Artery and Recurrent Patterns in Location, Orientation, and Rupture Status of Lateral Aneurysms: an Image-Based Computational Study", Neurosurgery, vol. 68, Issue 5, May 1, 2011, pp. 1270-1285.

Tutino, et al., "Aneurysmal remodeling in the circle of Willis after carotid occlusion in an experimental model", Journal of Cerebral Blood Flow & Metabolism, 34, 2014, pp. 415-424.

\* cited by examiner

METHOD AND SYSTEM FOR CLASSIFYING AN INDIVIDUAL AS HAVING OR NOT HAVING DISPOSITION FOR FORMATION OF CEREBRAL ANEURYSM

TECHNOLOGICAL FIELD AND BACKGROUND

This invention is in the field of medical devices and relates to a method and system for monitoring a condition of aneurysms in individuals.

An aneurysm is a localized, blood-filled balloon-like bulge in the wall of a blood vessel Aneurysms in the arterial tree of the brain, called, cerebral aneurysms, or Berry aneurysms typically cause no symptoms when they form, A brain aneurysm may rupture and cause an intracranial hemorrhage (called subarachnoid hemorrhage). Once ruptured, aneurysms cause high rates of morbidity and mortality. Depending on the severity of the hemorrhage, brain damage or death may result. Almost half afflicted individuals die in one month, while third of survivors, have moderate to severe disability. Cerebral aneurysms are not congenital, but rather develop during life. Besides age, known risk factors, for aneurysms development include female gender, familial preponderance, polycystic kidney disease, the presence of atherosclerotic disease, smoking, and hypertension.

WO2014077360 discloses a system including a memory, an aneurysm identification device, a distortion-degree evaluation device, and a rupture risk derivation device. The memory stores medical image data. The aneurysm identification device identifies an aneurysm in the medical image data. The distortion-degree evaluation device quantitatively evaluates a distortion degree of the aneurysm. The rupture risk derivation device derives a rupture risk of the aneurysm from a result of the evaluation.

WO2011008906 discloses a computer-aided system which identifies aneurysm suspects in 3D image datasets. The system takes the raw image dataset as input and assigns one or more points of interest (POIs) in the image data. The system determines one or more features for each POI and identifies one or more aneurysm suspects from among the assigned POIs based on the determined features.

WO2010121146 discloses an approach to automatically detecting, classifying and/or highlighting abnormal structures such as brain aneurysms is based on three-dimensional studies of the brain vessels. The approach is applicable to effectively all currently available modalities of acquisition of the cerebral vessels, including magnetic resonance angiography (MRA), computed tomography angiography (CTA), and conventional catheter-based three-dimensional rotational angiography (3DRA).

Laurie A, et al., (J Biomech 22, 3018-3027; 2014) described the curvature effect on hemodynamic conditions at the inner bend of the carotid siphon and its relation to aneurysm formation.

Tutino Y M, et al., (*Journal of cerebral blood flow and metabolism* 34, 415-424; 2014) showed that increased blood vessel tortuosity preceded aneurysm formation following bilateral carotid ligation in rabbit models.

Piccinelli M, et al., (*Neurosurgery* 68, 1270-1285; 2011) pointed to a correlation of the presence of sharp bends in feeding arteries with aneurysm rupture.

Kayembe KN, et at, (*Stroke* 15, 846-850; 1984) previously described a correlation between variations in the Circle of Willis (a ring at the base of the brain where basilar artery and the internal carotid arteries "communicate" with each other) and an increased risk for developing cerebral aneurysms.

GENERAL DESCRIPTION

There is a need in the art for a novel technique enabling effective identification of individuals with a high risk for aneurysm formation.

The present invention provides a novel and powerful technique for identifying individuals with a predisposition for developing aneurysms before, even years ahead of aneurysm's development. The identification of the possibility to developing future aneurysms gives opportunity to prevent the development of aneurysms and saves the population from its devastating consequences.

It is noted that the invention focuses on cerebral aneurysms and Saccular aneurysms in particular. Therefore, wherever in this specification, the following are interchangeably and equivalently used: "aneurysms", "cerebral aneurysms", "intracranial aneurysms", "Saccular aneurysms" and "Berry aneurysms".

According to the invention, a noticeable difference in the morphology of the arterial network between healthy individuals and aneurysm-developing individuals is present. Herein below, some non-limiting quantitative methods/parameters that help in discriminating between the healthy and unhealthy individuals are described. However, the invention is not limited to one method or another. Any method that identifies the noticeable differences, e.g. automatic morphological comparison of the arterial tree of an individual, to that of another individual, can be used.

The invention can be utilized to map or screen large populations, without any need for background aneurysm-related information, in order to identify people with risk for developing cerebral aneurysms, and consequently save lives and lower drastically the so high economic and social burdens associated with the rupture of aneurysms.

The technique of the invention provides for simple, direct measurement of predetermined geometrical parameters of the artery in a healthy individual (i.e. not aneurysm patient) and provides meaningful results as to whether to classify the individual as having disposition for future aneurysm formation or not. On the other hand, the invention can also be used on individual that were/are diagnosed with aneurysms.

According to the novel technique of the invention, the screening of the large populations may be done for one time only, providing meaningful results for classifying the individuals as lacking or having risk for developing aneurysms in the close or far future. The classification of an individual as lacking or having disposition for future aneurysm development is done, according to the invention, with very high prediction certainty. Therefore those individuals who are classified as aneurysm-risk free can continue with their lives normally not worrying about this issue again.

On the other side, individuals classified as having the very high, almost certain, risk for aneurysm development can then be monitored periodically to detect any initiation of the life-threatening aneurysm(s) as early as possible and be treated suitably. Treating individuals in order to prevent development of aneurysms is far more safe and effective than treating people who have already developed aneurysms. Generally, aggressive blood pressure and heart rate control, in people who have the risk for developing aneurysms, may delay or even prevent aneurysm development. In contrast, people who already have developed aneurysms are nowadays treated, as long as the aneurysms have not ruptured, with invasive techniques (with all the risk this intervention carries), such as inserting metal coils into the aneurysm dome. These coils cause thrombus formation inside the aneurysm, thereby minimizing rupture risk.

The inventor has found that there is a correlation between arterial three-dimensional (3D) geometry and the presence of aneurysms in an individual. Further, the 3D geometry of the arterial tree is a crucial risk factor for the formation of aneurysms. Individuals who are susceptible for developing aneurysms have arterial tree morphology which is markedly different than that of normal individuals. It is noted that the formation of aneurysms is not distributed randomly but rather follows certain rules with defined parameters. Aneurysms develop in areas with complex configurations, for example at bifurcations fulfilling some conditions as will be detailed herein below.

According to the invention, several factors relating to the characteristics of the artery are crucial for aneurysm development. These factors include, inter alia, presence of flow-diverting regions/locations, such as sharp bends, along the artery; size (diameter) of the artery at the flow-diverting location; the artery wall condition at the flow-diverting location and location of the artery in the body.

As noted, the location of the artery is a first parameter influencing the formation of aneurysms. The vast majority of aneurysms arise in the intra-dural compartment (the compartment just below the brain and above the skull base). Cerebral arteries have very tortuous path before reaching the lower surface of the brain (while inside the bony skull, and the cavernous sinus). Although cerebral aneurysms may arise in this tortuous path (outside the dura), they are quite rare, and in most instances do not rupture. While the invention is not limited to the intra-dural region or even the brain, and it may be practiced with suitable customization to other arteries in another organs of the body, the invention focuses on the cerebral arteries in the intra-dural compartment.

The size of the artery, which is generally expressed by the artery diameter or radius (of the transverse cross-section of the artery), is a second parameter. The numbers which are given herein below refer to the internal diameter/radius, as this what the imaging modalities used by the inventor give. However, it is noted that this should not limit the invention and the numbers can be adapted for the external diameter/radius as the case may be. The inventor has found that Saccular aneurysms arise from medium-sized arteries. Smaller sized arteries do not develop Saccular aneurysms. In particular, cerebral arteries with a diameter less than 1 mm (so-called "hypoplastic" or underdeveloped), are considered as small arteries which do not develop aneurysms. Considering the intra-dural region of the brain, arterial diameter of arteries upon joining the lower surface of the brain is about 5~6 mm, and this diameter goes down along the artery. Consequently, the main range in which aneurysms develop in the subarachnoid space is from about 1.3 mm to about 6 mm for the internal diameter.

Another important parameter that dictates the development of aneurysms is the 3D morphological curvature of the artery, such that both the curvature value and the curve direction, i.e. the direction into which the flow is changing its direction, have been found to play significant roles. The inventor has found that cerebral aneurysms develop in a flow-diverting region along the arteries, with high curvature peaks resembling sharp bends in the itinerary of the artery.

According to the novel technique of the invention, the artery cross-sectional size (its diameter/radius) and the curvature value, at the flow-diverting location, that indicate whether the individual has a disposition for future aneurysm initiation and formation, are co-related. The upper bound/limit of the curvature value, which above it an individual develops aneurysm(s), is dependent on the artery size (diameter/radius), and/or vice versa. In one specific scenario, the relation between the artery size and the curvature upper limit value is a one-dimensional relation, more specifically a direct, linear, relation. The artery size dictates the upper limit value of the curvature, such that for different artery sizes, above the predetermined minimal value, corresponding different upper limits for the curvature value exist. In other words, a specific upper limit of the curvature value can be indicative of aneurysm formation for a specific first artery size, while it will not be indicative of aneurysm formation for another specific artery size, typically larger than the first artery size.

It is noted that, the aneurysms develop mainly in an aneurysm direction opposite to the curve direction. The curve direction may be defined as the direction of a vector pointing in a normal direction to the tangent vector pointing in the direction of the flow inside the artery, at each specific point in the curve. The normal vector points towards the direction along which the tangent vector changes its direction. In another words, the normal vector is defined as the derivative of the tangent vector with respect to the arclength parameter of the curve. The Frenet-Serret frame system could be used with the invention with the same nomenclature to facilitate understanding, i.e. the tangent vector and the normal vector of the Frenet-Serret frame are the same as the tangent and normal vectors described herein above. The calculation of the curvature of the artery may be done by calculating the curvature of a centerline of the artery. The centerline is defined as the line composed of the centers of spheres inscribed in the artery at each point along its axis, sequenced by flow direction.

The aneurysm develops only if an artery wall exists in the opposite to the normal vector direction as described above. Moreover, it has been found that aneurysms develop only in the maximal centrifugal forces region, on the convex, not concave, side of the curve.

Individuals with the above-mentioned factors develop aneurysms, in the high curvature region, while those who do not meet these criteria do not. In other words, as described above, there is a threshold of an upper bound/limit for the artery curvature, being dependent on the arterial size (diameter/radius), which is breeched by aneurysm-developing individuals but not breeched by healthy individuals who do not develop aneurysms. In normal, healthy, individuals the arteries turn in a smooth way keeping the curvature below a threshold of an upper limit. The diagnosis of aneurysm developing and non-developing individuals is unchanged when comparing individuals with larger head circumferences to those with smaller ones. It is similar in both sexes, and does not change with age.

In the invention, the definition of an artery includes the "parent" artery and dominant branches that bifurcate from it, at each bifurcation in the arterial tree. When an artery bifurcates to two or more branches, one of these "daughter" arteries is dominant, being the branch which diverts the flow of the parent artery. If there is no bifurcation, an aneurysm develops in the flow-diverting location along the artery. The parent artery's flow does not affect other branches which are considered as new parent arteries starting at the current bifurcation, the other branches are subject to similar rules as the parent artery from which they bifurcated. According to the invention, these rules apply to all daughter branches in every bifurcation.

As has been said, it is possible to test each individual, and to screen large populations, to find whether an individual has these arterial aberrations and may be susceptible (with very high possibility/disposition) to aneurysm formation.

Thus, according to one broad aspect of the invention, there is provided a method for controlling aneurysm initiation or formation in an individual, the method comprising:

receiving input data comprising morphological data of an artery comprising data indicative of at least first and second geometrical parameters of the artery along its trajectory;

analyzing the input data to identify at least one flow-diverting location along the artery satisfying first and second predetermined conditions of the at least first and second geometrical parameters; and classifying the individual as having or not having disposition for future formation of an aneurysm in a point on a wall of the artery, depending respectively on whether the at least one flow-diverting location is identified or not, and generating classification data; and generating, based on the classification data, prediction data for the individual with regard to future aneurysm formation.

It should be understood that morphological data includes data about geometry (in a 3D space) of an artery within a brain portion (e.g. at least an intra-dural brain portion). Such data about the artery is indicative of the geometry (size and shape) of the artery along its trajectory. The prediction for formation of an aneurysm is based on identifying one or more predetermined locations (having certain predefined properties) in the artery and analyzing the one or more locations to determine whether the geometrical data at the location satisfies a condition for aneurysm formation.

In some embodiments, receiving of the input data comprising receiving the first and second geometrical parameters comprising artery size and artery curvature along the artery's trajectory.

In some embodiments, the first and second predetermined conditions comprise respective first and second predetermined threshold values of the first and second geometrical parameters.

In some embodiments, analyzing of the input data comprises identification of the first predetermined condition of the first geometrical parameter as being a precondition for identification of the second predetermined condition of the second geometrical parameter.

In some embodiments, analyzing of the input data comprises identification of the first predetermined condition being a predetermined minimal value of the first geometrical parameter and identification of the second predetermined condition being a predetermined maximal value which below an aneurysm will not form and which above an aneurysm will form.

In some embodiments, the first and second predetermined conditions of the at least first and second geometrical parameters have a predetermined relation there between.

In some embodiments, the predetermined relation is a linear relation between the first and second geometrical parameters.

In some embodiments, the artery comprises each dominant artery branch bifurcating at each bifurcation site along the artery, the dominant artery branch being a branch which diverts the flow of the artery.

In some embodiments, the wall of the artery is at a convex side of the artery.

In some embodiments, the artery is a cerebral artery and the aneurysm is a cerebral aneurysm.

In some embodiments, the cerebral artery is located in an intra-dural brain region.

In some embodiments, the artery size has a diameter value of 1.3 mm or greater.

In some embodiments, analyzing of the input data comprises applying a Frenet-Serret frame analysis along a centerline of the artery, to thereby identify the at least one flow-diverting location along the artery. The centerline may comprise point centers of spheres inscribed in the artery. The centerline may be defined as a line with a direction defined by flow direction.

In some embodiments, the morphological data is obtained from image data indicative of a cerebral arterial tree. The image data may be indicative of a three-dimensional image of the cerebral arterial tree.

In some embodiments, the cerebral arterial tree comprises a plurality of cerebral arteries, each of the plurality of cerebral arteries starts at an entrance into intra-dural brain region or at a bifurcation site in the cerebral arterial tree.

According to another broad aspect of the present invention, there is provided a system for controlling aneurysm initiation or formation in an artery, the system comprises:

a data input utility configured and operable for receiving image data of the artery;

a data processing utility configured and operable for:
analyzing the image data and generating morphological data comprising at least first and second geometrical parameters of the artery at each point along its trajectory, identifying in the morphological data a flow-diverting location along the artery, the flow-diverting location along the artery having predetermined first and second conditions of the first and second geometrical parameters, and classifying the artery as having or not having disposition for future formation of an aneurysm in a point on a wall of the artery; and an output utility configured and operable to generate output data indicative of the classification.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
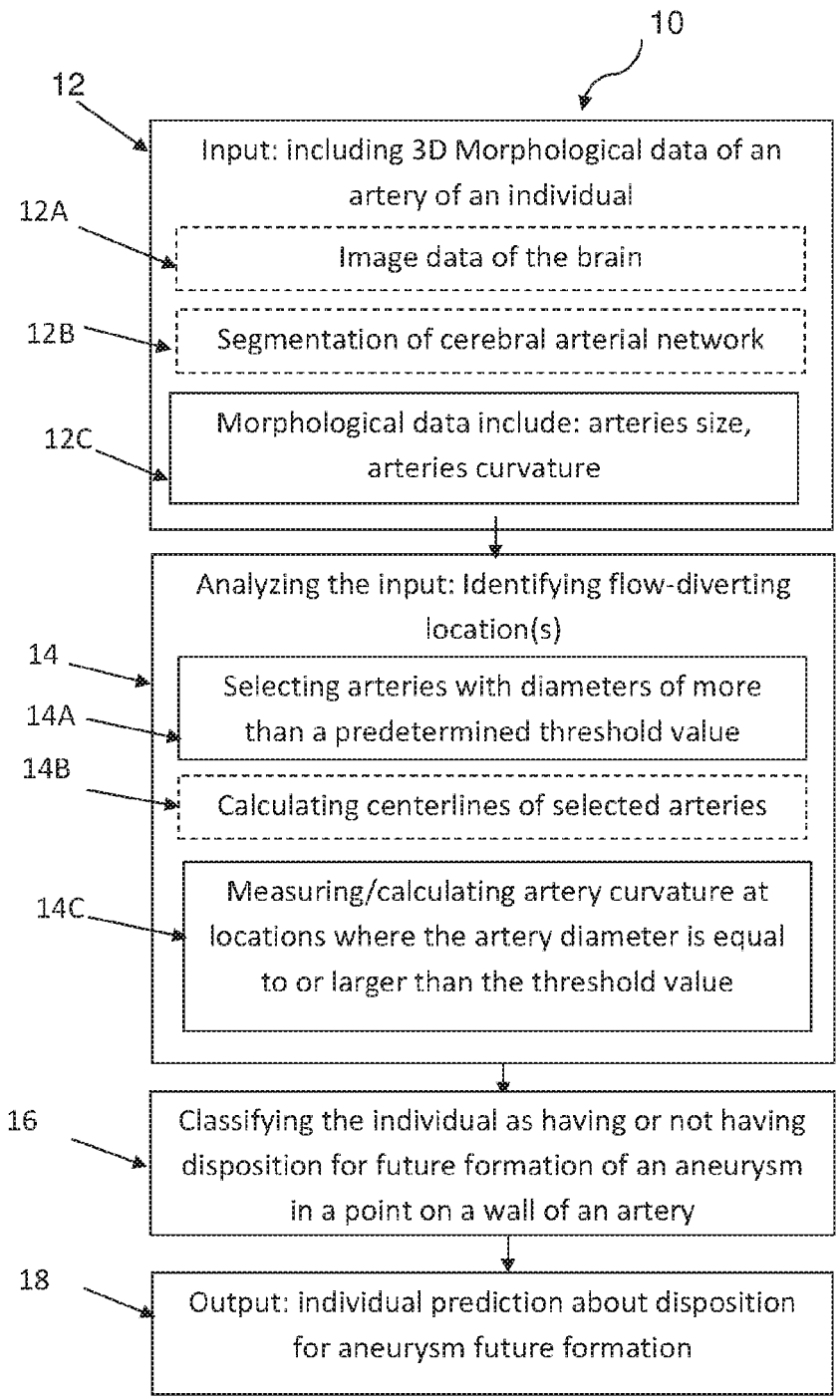
FIG. 1A is a diagram flow illustrating one method in accordance with the invention.

Reference is made to FIG. 1A illustrating a method 10, according to the invention, for use in detection of disposition for aneurysm initiation or formation in an individual and classifying the individual as having or lacking disposition for aneurysm future formation. The method 10 includes, inter alia, examining an artery to identify a condition for predicted formation of an aneurysm in the artery. The method 10 exemplifies the invention being applied to the cerebral arteries. It should be noted, however, that the method could be applied to another artery or artery network/tree in the body with appropriate adjustment of the values of parameters which will be described herein after. The method includes, inter alia, the steps of obtaining input including morphological data of the artery (step 12); analyzing the input data to identify at least one flow-diverting location along the artery (step 14) being stress-concentration region (s); classifying the individual as having or not having disposition for future formation of an aneurysm in a point on a wall of the artery (step 16); and generating output prediction data about the individual with respect to disposition for aneurysm future formation (step 18).

In the figure, optional and/or non-limiting exemplary steps and/or steps that can be performed with various modalities not necessarily described herein and which do not form part of the invention, are highlighted with dashed boxes.

It should be understood that, the input data including the morphological data belongs usually to an individual with no known aneurysm-related past, i.e. the individual is any person in the population. The invention is directed at revealing those who have a disposition for aneurysm formation. However, the invention can be equally practiced on individuals with aneurysm-related past, such as individuals who had or have aneurysms.

The acquisition of the input data of the individual, including the morphological data (step 12) can be done by utilizing image data of the brain (step 12A) which can be obtained by known methods in the art, including but not limited to computed tomography (CT), magnetic resonance imaging (MRI), both of which can be used with a contrast specified agent(s), and cerebral angiography. It should be noted that the acquisition of the image data is not part of the invention, and the invention is not limited to the above mentioned modalities and it can be used with any modality, known or will be developed in the future, for obtaining morphological data of the concerned artery tree, as long as the modality gives a three-dimensional (3D) image data or morphological data.

As said, while this does not the limit the invention, the focus in the described method is made on the brain artery tree and more specifically the artery network of the intra-dural compartment of the brain, as this is the compartment in which the majority of aneurysms develop. Generally, the image data (step 12A) includes data of different anatomical parts of the brain and not only the arteries, such as the veins and the brain tissue. In this case, a segmentation procedure (step 12B) is carried out in order to isolate the data relating to the arterial network from the data relating to all other anatomical figures in the brain which are irrelevant for the aneurysm analysis.

As will be described further below, the morphological data (step 12C) of interest for the subsequent analysis step (step 14), includes such geometrical parameters as the artery(ies) size(s) along the artery trajectory and the artery (ies) curvature value(s) along the artery trajectory. The artery size parameter can be represented by its diameter or radius along its trajectory.

After acquisition of the 3D morphological data of the artery/artery network in the intra-dural compartment, the diameter(s) of the arteries in the artery network is determined and those arteries with a diameter being above a predetermined value are selected (step 14A) for further analysis, whereas the arteries with a diameter less than the predetermined value are dropped and excluded from further analysis. It is to be noted that, while this step of deselecting arteries (step 14A) is shown in the figure as belonging to the data analysis step (step 14), this step can be performed previously and already directly included in the input data provided (step 12). The inventor, as well as other researchers in the field, have found that arteries with a diameter of 1 mm or less do not develop aneurysms. Since the arteries entering the intra-dural compartment have a diameter of about 5~6 mm at the entry point, for the purposes of identifying formation of cerebral aneurysms, the lower and upper threshold values for artery selection is chosen to be in the range of about 1.3-6 mm. It should be noted, that for aneurysms in arteries in other in parts other than the intra-dural compartment the range changes accordingly. While, the inventors have not checked with other regions, the invention is not limited to the intra-dural compartment and to the above-mentioned range for artery selection.

After focusing on the arteries in the intra-dural compartment of the brain which have a diameter between 1.3-6 mm, the next important geometrical parameter for identifying the disposition of an individual to develop aneurysm(s) in the wall of an artery is the artery's curvature. The three-dimensional curvature is a well-established geometrical parameter and can be measured by different known techniques. Further below, additional details about the specific technique which was used by the inventor can be found. One non-limiting example of a way to calculate the curvature of the arteries is by optionally computing and drawing their centerlines (step 14B) as will be further described below.

As described above, at each location along the artery where the diameter fulfills a predetermined artery threshold value, e.g. being at least about 1.3 mm, the artery curvature at that specific location is measured/calculated to look for a curvature threshold value (step 14C). If the measured curvature value is equal to or exceeds the predetermined curvature threshold value, the individual is classified as having disposition for aneurysm future formation in the artery wall at the specific location along the artery where the two threshold values are met (step 16). And, if the measured curvature value is less than the predetermined curvature threshold value, the individual is classified as not having disposition for aneurysm future formation in the artery wall at the specific location along the artery (step 16).

Figure 2:
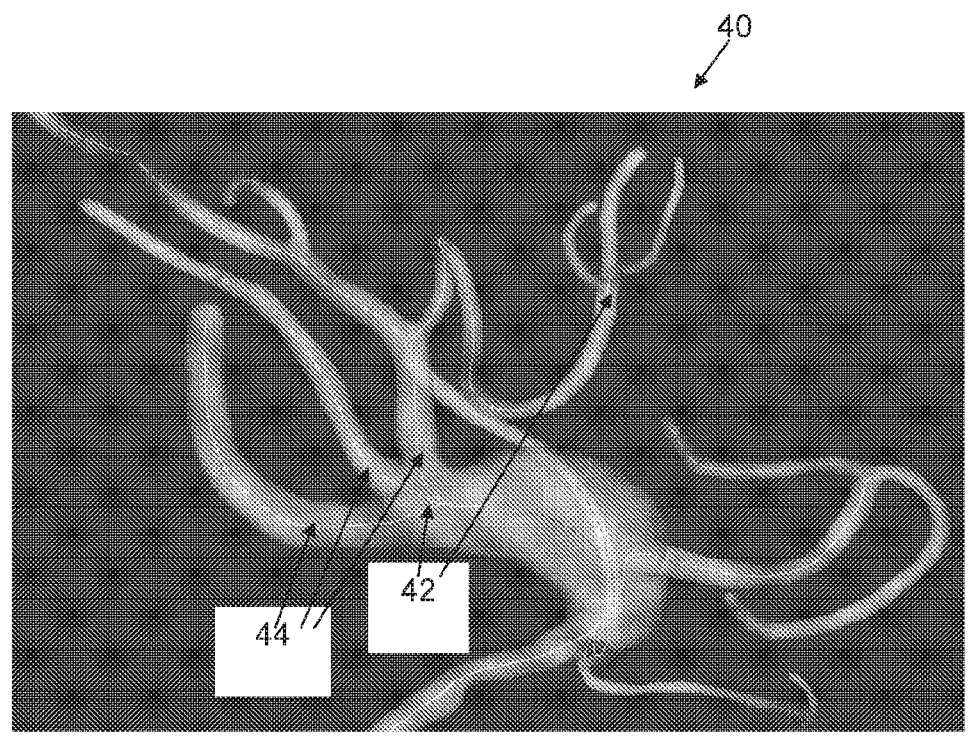
FIG. 2 schematically illustrates the method of centerlines calculated for an arterial network.

Reference is made to FIG. 2 illustrating an example of an artery network 40 having bifurcations, e.g. 42, with the centerlines 44 calculated and shown passing at the middle (center) along the longitudinal axis of each artery. The calculation of arterial centerlines 42, in this non-limiting example, is based on the "Voronoi diagram", which simulates inflating "balloons" inside the arteries with the balloons' centers being the centerlines of the arteries. Centerlines are powerful descriptors of the shape of vessels and are determined as weighted shortest paths traced between two external points. In order to ensure that the final lines are in fact central, the paths cannot lie anywhere in space, but are bound to run on the Voronoi diagram of the vessel model, considered as the place where the centers of maximal inscribed spheres are defined. Centerlines are determined as the paths defined on Voronoi diagram sheets that minimize the integral of the radius of maximal inscribed spheres along the path, which is equivalent to finding the shortest paths in the radius metric.

Figure 3:
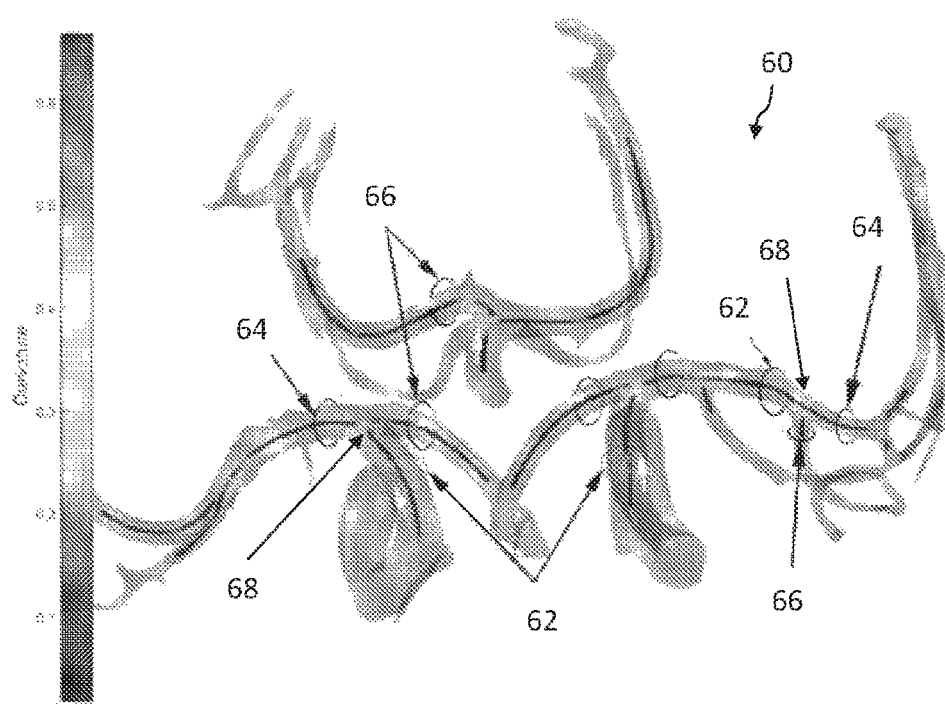
FIG. 3 schematically illustrates analysis of an arterial network including parent arteries, dominant arteries and other arteries.

A typical artery tree would contain bifurcations at which a specific artery splits into several other branches stemming out of the bifurcation. Referring to FIG. 3, there is shown an example of an artery network 60, containing several bifurcations 68. According to the invention, during the calculation of the centerlines, the arteries at each bifurcation are analyzed and divided to three artery categories. At each bifurcation, the entering "parent" artery 62 splits into two kinds of "daughter" arteries, a "dominant" artery 64 and "secondary" (or "other") arteries 66. The "dominant" artery 64 is the main branch bifurcating from the "parent" artery 62, into which the main blood flow diverts. During the calculation of the centerlines in the artery network, the centerline of the parent artery 62 continues into the dominant artery 64. Therefore, the dominant artery 64 is considered as a continuing part of the parent artery 62 which entered into the bifurcation 68. The secondary artery 66 (one or more) is considered as a new independent artery starting at the bifurcation and analysis is carried on it as a new parent artery. Therefore, a new centerline starts for the secondary artery at the bifurcation and at each new bifurcation this secondary parent artery splits again into a dominant artery being its continuation and at least one new secondary artery.

Turning back to FIG. 1A, one non-limiting example for measuring/calculating the curvature by utilizing centerlines is described. In step 14B, the centerlines are processed and the curvature of the three-dimensional centerlines is calculated to identify flow-diverting locations, i.e. sharp bends with certain characteristic as will be described below, along the artery network.

The curvature of a regular space curve C in three dimensions (and higher) is, as in the case of curves in two dimensions, the magnitude of the acceleration of a particle moving with unit speed along a curve. Thus, if $\gamma(s)$ is the arc length parameterization of C then the unit tangent vector $T(s)$ is given by: $T(s)=\gamma(s)$ The curvature is the magnitude of the acceleration:

The direction of the acceleration is the unit normal vector $N(s)$, which is defined by:

The plane containing the two vectors $T(s)$ and $N(s)$ is called the osculating plane to the curve at $\gamma(s)$. The curvature has the following geometrical interpretation. There exists a circle in the osculating plane tangent to $\gamma(s)$ whose Taylor series to second order at the point of contact agrees with that of $\gamma(s)$. This is the osculating circle to the curve. The radius of the circle $R(s)$ is called the radius of curvature, and the curvature is the reciprocal of the radius of curvature:

The tangent, curvature, and normal vector together describe the second-order behavior of a curve near a point. In three-dimensions, the third order behavior of a curve is described by a related notion of torsion, which measures the extent to which a curve tends to move in a helical path in space. The torsion and curvature are related by the Frenet-Serret formulas (in three dimensions) and their generalization (in higher dimensions). As these centerlines consist of discrete points, and curvature is not defined for discrete points, the centerline curvature is defined based on finite difference.

As described above, the inventor has found that the curvature value should not exceed a predetermined threshold (upper bound) value in normal people, and wherever the curvature value is equal to or exceeds the predetermined threshold (upper bound) value, then if one more condition is met as will be described further below, an aneurysm will develop at the sharp bend location.

When both above-described conditions are met, i.e. the diameter of the artery and the curvature peak value (measured for example along the centerline) are equal to or above the respective threshold values, the Frenet-Serret frame can be applied to that point (at the flow-diverting location) in order to obtain information about the curve direction/location (point) on the artery wall where the aneurysm will develop, which is given by the opposite direction to the direction of the normal vector of the Frenet-Serret frame. The normal vector is the vector normal to the flow direction. According to some non-limiting embodiments of the invention, an examination is carried out in the direction opposite the direction of the normal vector to check if an artery wall resides in the direction opposite the direction of the normal vector. If the check is positive, then the location of the point on the artery wall at which a vector opposite the normal vector intersects with the artery wall is marked as a location of future aneurysm development. The location of the intersection point resembles the way the flowing blood would go out of the itinerary because of the sharp curve. It is also clear, that if an aneurysm already exists in that direction then the invention provides also a way to detect existing aneurysms as well. However, if the vector opposite the normal vector points in a direction where a branch at a bifurcation starts, then no aneurysm will form and the blood will flow into that branch.

Figure 4:
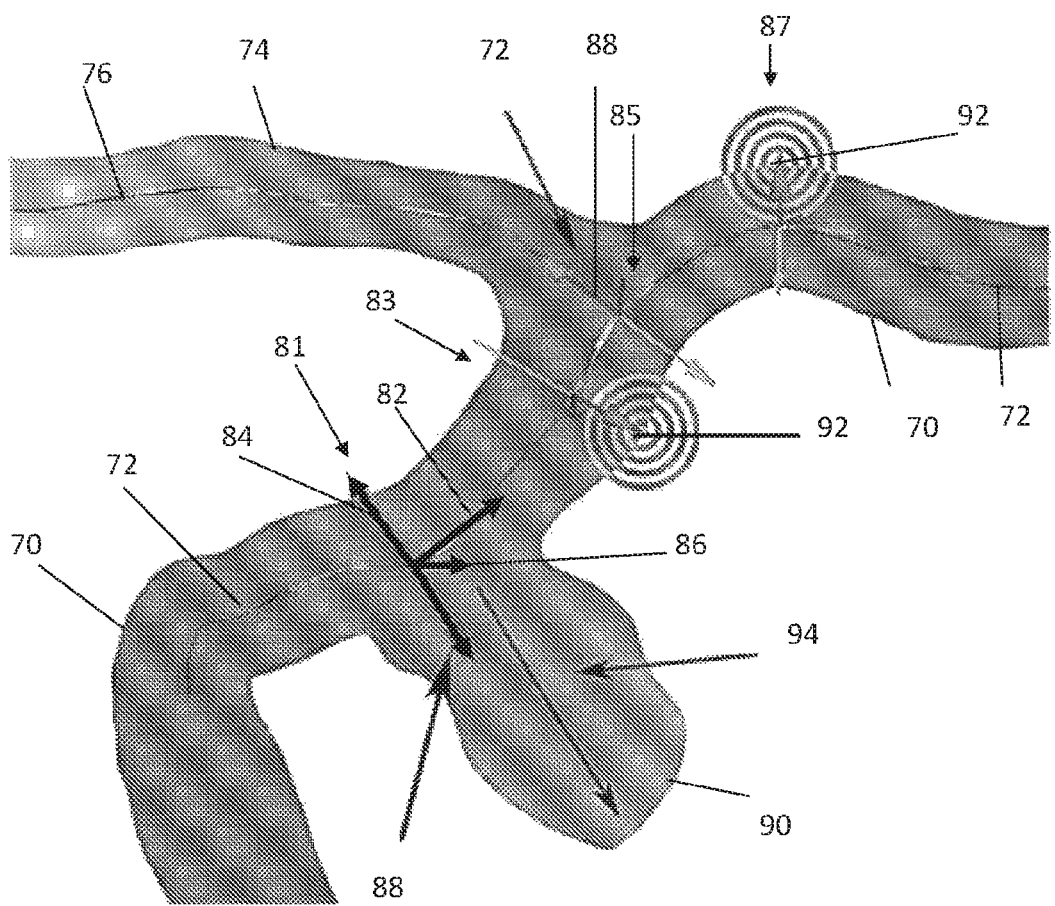
FIG. 4 schematically illustrates application of the Frenet-Serret frame to an arterial network.

Reference is made to FIG. 4 illustrating the application of the Frenet-Serret frame analysis to the centerlines of an exemplified artery 70 with a blood flow going upwards and to the right and left side of the figure. As shown, the centerline 72 passes roughly along the central axis of the artery 70 which at a bifurcation 74 bifurcates into two branches, a dominant branch 70 (to the right side) and another secondary branch 74 (to the left side) that is regarded as a new artery subject to a new analysis according to the invention, with its own centerline 76. The Frenet-Serret frame is applied along the centerlines 72 and 76. In the figure, the Frenet-Serret frame is applied at four exemplary points 81, 83, 85 and 87. In practice, the Frenet-Serret frame may be applied at each point along the centerline. Alternatively, seeking to save effort and time, the frame is applied only at points of the centerline having a curvature value peak of at least 0.3 mm$^{-1}$ (for arteries in the intra-dural compartment).

As illustrated, at each point along the centerline, the Frenet-Serret frame includes 3 vectors, the tangent vector 82 pointing in the direction of the blood flow, the normal vector 84 pointing in the curve direction, i.e. the direction of change in the direction of the tangent vector 82 (and being in the same plane with the tangent vector), and a bi-normal vector 86 pointing in an orthogonal direction both to the tangent and normal vectors such that it is the cross product of the tangent and normal vectors. According to the invention, a forth opposite vector 88 which points in the opposite direction to the normal vector 84 (and being in the same plane with the tangent and normal vectors) points in the direction of an already developed aneurysm, or a future-developing aneurysm if and only if an artery wall is present in the opposite vector direction. As mentioned earlier, an aneurysm would form only if the first condition applies, i.e. if the curvature value is above the predetermined curvature threshold value.

In the specific Frenet-Serret frame examples shown, the frame at location 81 illustrates an already formed aneurysm 90. The aneurysm's axis 94, along which the aneurysm 90 has developed, points in the same direction of the opposite normal 88. The frames at locations 83 and 87 illustrate two examples of two locations at which an artery wall 92 is present in the direction at which the opposite vector points. In both these locations (83 and 87), an aneurysm will develop, given that the condition of the curvature value, which depends on the artery size, is met (e.g., a curvature value of at least 0.3 mm$^{-1}$ in the intra-dural compartment). In the frame at location 85 (at the bifurcation 72), the opposite normal vector points in the direction of the secondary artery 74, there is no artery wall in the direction pointed to by the opposite vector 88 and therefore no aneurysm would develop at the location 85, even if the curvature value is 0.3 mm$^{-1}$ or higher.

As mentioned above, one possible way is to check all cerebral vasculature in the predefined arterial size (e.g. diameter) ranges and locations, and for every point in arterial centerlines to look for high curvature points, and whenever a high curvature value is detected, checking whether an arterial wall is present in the opposite to the normal vector direction. Mostly, it is difficult to notice these elbow points. The sharp bend is usually less than 2 mm long and most 3D reconstruction algorithms smooth it away. This fact makes it crucial for a system/tool to detect this sharp bend. Another advantage to this system is its ability to diagnose small aneurysms Small aneurysms are difficult to diagnose by experienced neuro-radiologists because they are only few voxels in diameter. In fact, the sensitivity for detecting aneurysms smaller than 5 mm, using an MRI, is less than 50%. The present invention solves this problem by looking for sharp bends, not aneurysms, and hence, it is able to detect these small abnormalities. Another way to appreciate these sharp bends, in most individuals, is by registering (aligning) one arterial 3D reconstruction to another. Registration of these two datasets makes the difference between a sharp bend and a low curvature in normal individuals visible to the naked eye.

Figure 1B:
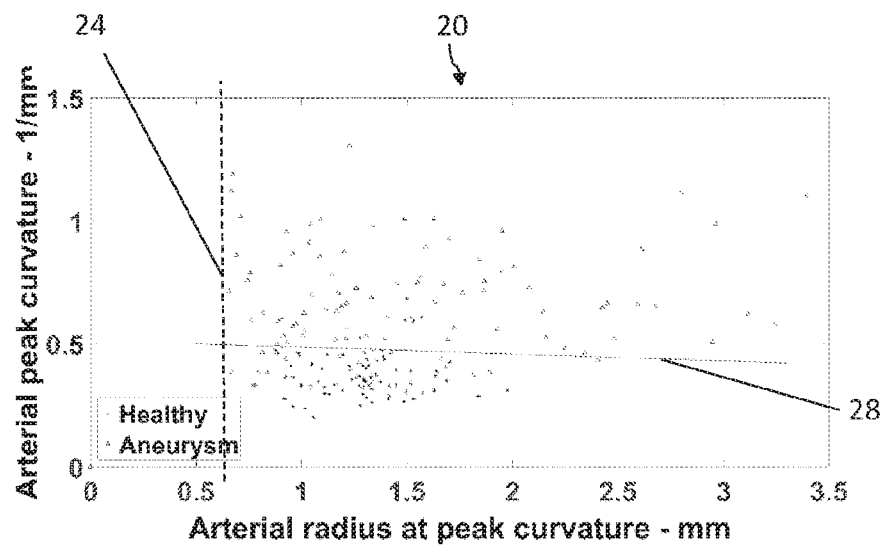
FIG. 1B illustrates classification of individuals based on geometrical parameters used in the method of the invention.

The inventor of the present invention has found that there is a relation between the artery size value and the artery curvature threshold value. According to this relation, a given artery size value determines the threshold value of the artery curvature, above which an aneurysm is most likely to develop, and under which no aneurysm will develop. Therefore, the threshold value of the curvature is dependent on the specific artery size (as long the latter is above the predetermined threshold value which is about 1.5 mm for the artery diameter). FIG. 1B illustrates the relation between the artery size and curvature parameters that was found by the inventor based on the method of the invention The graph 20 illustrates an artery size-curvature function 28 that describes the relation between the two geometrical parameters. In the figure, the graph 20 illustrates the arterial peak curvature (y-axis) plotted against the arterial radius (x-axis) in the same point/location along the artery. As shown, the threshold value for the arterial radius is about 0.65 mm, as shown by the illustrative line 24, above which an aneurysm may form and below which no aneurysm forms. As a result, the examination of the aneurysm formation is only done for arterial radius above about 0.65 mm. The figure illustrates the inventor's finding and conclusion that the relation between the artery size and the threshold value for the curvature is linear. The straight "Berry line" 28 is a function, which discriminates healthy from abnormal arterial configuration. Those above the line 28 are classified as having disposition for aneurysm formation while those under the line 28 are classified as healthy individuals that do not have disposition for aneurysm formation. The parameters of the straight line 28 are:

a=−0.28; b=0.515;

so, the line's function is:

(curvature threshold)=−0.28*(artery radius at the same point)+0.515.

According to the invention, the line 28 classifies people. For every individual, if the peak curvature point is identified and plotted against the radius at this point, then if the point is located above the line 28, the individual will develop an aneurysm, otherwise, the individual will not.

The line 28 yields:

Positive predictive value (PPV)=0.9432; and

Negative predictive value (NPV)=0.8913.

This means that the line 28 has a very strong classifying indication.

Figure 5:
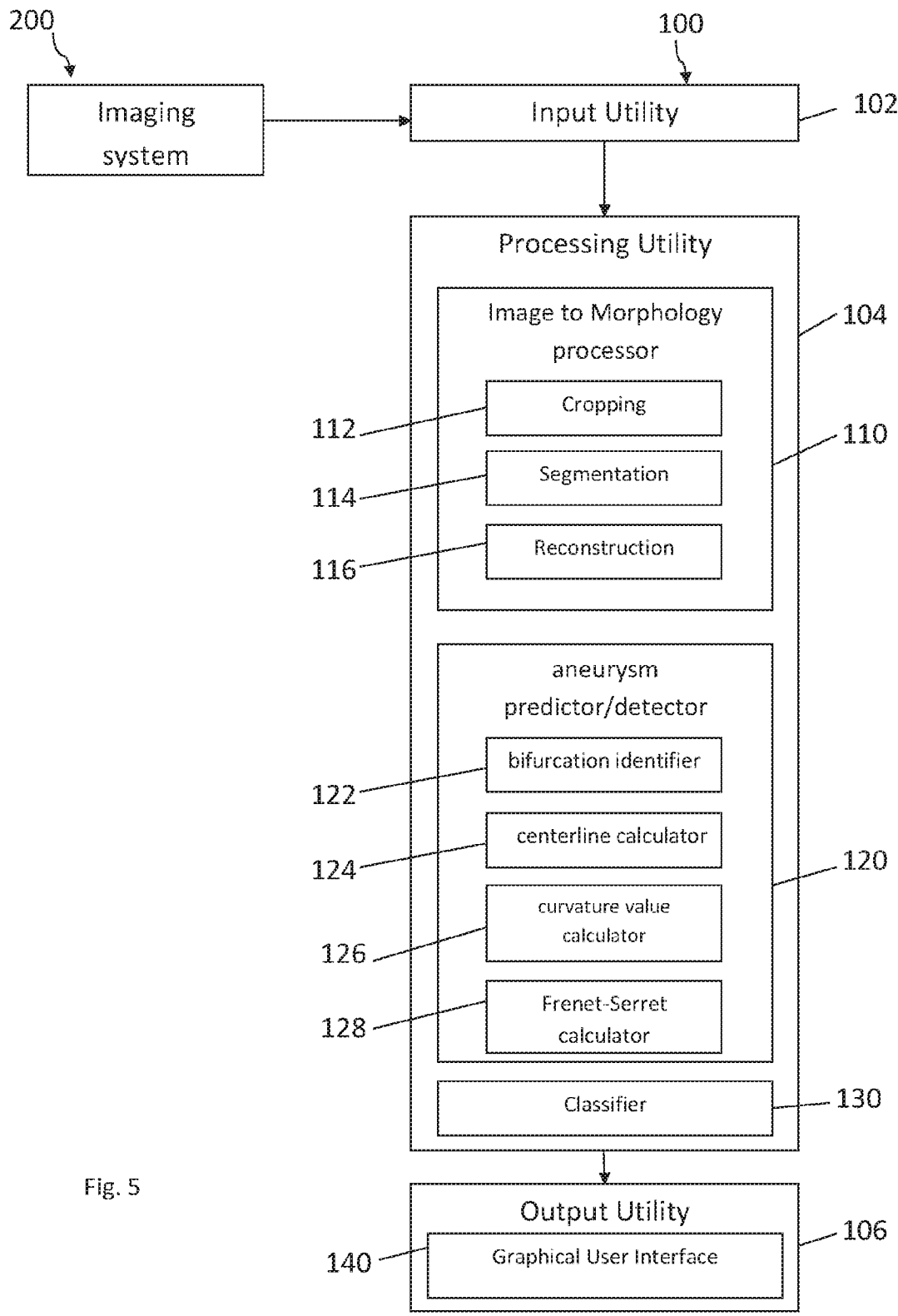
FIG. 5 schematically illustrates a system in accordance with the invention.

Reference is made to FIG. 5 illustrating one non-limiting example of a system configured according to the invention. The system 100 can be configured with a variety of elements configured and operable to perform the method described above. It should be understood that the below described example is one among many that can be used according to the invention. The system 100 is generally a computerized system (software or hardware or both) which includes at least the following modules and utilities: an input utility 102 for receiving input image data from a suitable imaging system 200; a processing utility 104 for analyzing the input image data, by utilizing, inter alia, the method of the invention, as described above; and an output utility 106 for outputting data to the user. In some embodiments, the imaging system 200 may form an integral part of the system 100. However, generally, the imaging system is an independent system providing image data to the system 100 via its input utility 102. The output utility 106 may include a graphical user interface/display 140 for presenting the processing utility 104's output(s) to the user. In some embodiments, the output utility 106 may include a speaker for delivering suitable sound alerts to the user.

The processing utility 104 includes modules configured to process the input image data to eventually find locations along the arterial walls at which a future aneurysm will develop. Possibly, also to find locations of already developed aneurysms, especially small developed aneurysms which might be difficult to diagnose by the current known imaging methods and systems. Each of the modules may be software configured to run on a dedicated hardware. Alternatively, the modules may be independent pieces of software configured to run on a regular computer.

The processing utility 104 is configured and operable to analyze the image data to extract the morphological data of interest, including at least geometrical parameters as the artery's size and curvature at each point along the artery; analyze the geometrical parameters, such that at each point along the artery, for every artery size above a predetermined threshold value (e.g. 1.3 mm), check whether the artery curvature at that point fulfills the artery size-curvature function, described above in FIG. 1A; and classify the individual as having or no having disposition for future aneurysm development based respectively on whether the curvature value satisfies the curvature's threshold value, as acquired by the artery size-curvature function, or not. Below, different modules of the processing utility to achieve its purpose are described.

The first module 110 is an "image to morphology data" processing module which receives as an input the image data and outputs as an output the morphological data and possibly three-dimensional reconstructed image/artery model. The image to morphology data module 110 includes various sub-modules such as cropping 112, segmentation 114 and reconstruction 116 sub-modules. The cropping 112 of the image data is performed as needed, keeping only the relevant image data of the specific region of interest in the body, e.g. the circle of Willis and calculating the diameter of arteries to keep arteries larger than 1.3 mm in diameter. The image to morphology data module 110 then performs segmentation 114 of the cropped data, if needed, i.e. to remove all non-artery tissue. Then, the image to morphology data module 110 performs three-dimensional reconstruction 116 of the segmented data such that a three-dimensional model of the artery network could be presented via the output utility, together with aneurysm data as will be further detailed below.

The second module 120, the aneurysm predictor/detector, can include such sub-modules as bifurcation identifier 122, centerline calculator 124, curvature value calculator 126, and Frenet-Serret calculator 128. The bifurcation identifier 122 receives the morphological data and identifies bifurcations in the artery network. The centerline calculator 124 then computes the centerlines of the arteries in the artery network by identifying, at each bifurcation, the parent artery (the one entering the bifurcation according to the blood flow direction), the dominant branch forming a continuation for the parent artery and each secondary branch stemming out of the bifurcation thus forming a new parent artery to which the analysis is carried out independently. The curvature value calculator 126 then calculates values of the centerline's curvature to enable identifying flow-diverting locations having curvature values falling within the required range. This is done in as short as possible step distances along the centerlines. The curvature value calculator is configured to utilize the arterial size-curvature function, as described in FIG. 1A, to thereby determine the threshold curvature value for each artery size along the artery's trajectory. The Frenet-Serret calculator 128 applies the Frenet-Serret frame to the points identified with curvature values higher than the threshold value and computes the opposite normal vector to thereby identify the presence of an artery wall in the path given by the opposite normal vector's direction. If a wall exists, then aneurysm(s) will form and the opposite.

Eventually, the processing utility 104 marks the locations of future aneurysms along the artery walls, and the output utility 106 outputs the three-dimensional constructed artery network, the centerlines, the Frenet-Serret frame and the locations on the artery walls susceptible for aneurysm formation to the user.

The classifier 130 is configured and operable to receive the analysis data as processed by the module 120 and generate classification data about the individual that include the individual's disposition for developing aneurysm(s) at each potential location in his brain arterial network. If more than one potential location is identified, the classifier 130 is configure to rank the plurality of potential location based on the severity and/or time-expectancy for developing aneurysm at each of the potential locations. Consequently, the classifier 130 can be configured to generate recommendation data about the recommended frequency of monitoring the individual having the disposition for aneurysm formation, based on the number and/or severity of the individual's diagnosis.

The inventors have performed experiments to validate the technique of the invention. Model validation and statistical analysis were performed using online available datasets of normal individuals, compared against those of patients harboring cerebral aneurysms. Morphological data was obtained from brain images (step 12A in method 10). Normal datasets were composed of MRI brain images of healthy volunteers. These were comprised of images of the brain of subjects in which 20 patients were scanned per decade (18-29, 30-39, 40-49, 50-59, and 60+), with each group equally divided by sex. The datasets used, were of brain Magnetic Resonance angiography (MRA) acquired at 0.5×0.5×0.8 mm3. MRI images were first cropped, using a software tool, keeping the circle of Willis and arteries larger than 1.3 mm in diameter. The second step was segmentation (step 12B, removing all non-artery tissue). MRA was segmented based on voxel intensity, using single threshold. This step was implemented using the same tool (a software), used for cropping. Following segmentation, a 3D reconstruction of the circle of Willis, was performed using the Vascular Modeling Toolkit (VMTK). These 3D reconstructions were compared against 102 datasets provided by the Aneurisk project. Ten datasets, in which the aneurysm involved more than half the parent artery circumference, were excluded. Mean age for the aneurysm group was 53.9; there were 62 females and 37 males. 55 of the cases were of ruptured cerebral aneurysms, while 43 were unruptured. Individual ages were 26-85. Most aneurysms (93%) were located in the anterior circulation, while 7% were in the posterior circulation (The basilar artery or the posterior cerebral arteries). This corresponds to aneurysms distribution by location, in the general population, with more than 90% of aneurysms located in the anterior circulation. The tool used to analyze arterial centerlines (step 14B), is the VMTK, which is a collection of libraries or image-based modeling of blood vessels. The VMTK is an open source tool, and was used in numerous studies in the past. The VMTK takes as an input the MRA images, or 3D reconstruction of cerebral arteries from any other modality and calculates arterial centerlines. Since sharp bends are very short (Mean: 0.779 mm, STD: 0.461), the centerlines were resampled to a resolution of 200 samples per mm. The inventors found this number to give the best results for the curvature estimation. Overall, more than 30 million point curvatures were calculated for both groups. Since 1D representation, of arterial curvature, using arterial centerline, simplifies calculations, the inventors performed all calculation on arterial centerlines.

Arterial 3D curvature (kappa or k) is a basic term in differential geometry, and it correlated with cerebral aneurysms initiation. One of the issues with calculating arterial curvature peaks, lays in the fact that arterial curvature is derived from the centerline's first and second derivatives, and these are very sensitive to noise. This fact is amplified by the fact that, MRA data is composed of discrete points (a grid of 3D points or voxels) and 3D arterial curvature is a continuous measure. Various low-pass filters were applied to vessel centerlines to mitigate digitization errors, these are ultimately arbitrary and affect the value of the curvature obtained; the more severe the filtering, the smoother the centerline and the lower the measured curvature. Using less aggressive filter falsely identifies noise as sharp bend in arterial geometry and does not allow true arterial curvature peaks to be isolated. In addition, the inventors used two different imaging modalities for curvature estimation, while keeping the processing algorithm the same. This step was taken in order to preserve the curvature difference between the two groups. For this reason, the same smoothing parameters were used for both groups. The inventor calculated the centerlines on aneurysms datasets, with the aneurysm in place. The VMTK calculates the centerlines based on the Voronoi diagram and fits a maximum inscribed sphere in the artery, whose center is the centerline's points. As long as there were, at least half the Original artery left, the VMTK is not significantly affected by aneurysms presence and the filtering process smooths the noise introduced away. Since arterial curvature and torsion determine its path, these sharp bends cause marked deviation of a cerebral artery, in the arterial segment, past the curvature peak (unless there is a second peak, which compensates, found in about 3% of cases). This is visible to the naked eye, by registering an aneurysm sequence to a normal one. This fact was used to validate the technique of the invention. Whenever there arises a doubt regarding the smoothing or reconstruction algorithm, a registration of the current dataset to another dataset, makes the difference visible.

Curvature peaks in arterial regions, where there is no vessel wall to be influenced by flow diversion, were excluded. The tool described, calculates the normal vector in each arterial curvature peak region, and checks to see if arterial wall exists in the opposite normal vector direction.

Calculated maximal 3D curvatures ($mm^{-1}$) were recorded for all datasets, as well as curvature peak length (mm) for curvature peaks larger than 0.3 $mm^{-1}$. Mean curvature peaks for all normal datasets was compared against the mean curvature peak, for all included aneurysms datasets. Student T test was used to compare the two peak curvature means.

Thus, the invention provides novel system and method for predicting future aneurysm formation. According to the invention, when several conditions are met an aneurysm will form. The conditions include value of size of the artery (typically, about 1.3 mm or more); curvature value of the centerline/wall of the artery is high (typically, 0.3 $mm^{-1}$ for cerebral arteries in the intra-dural compartment); and presence of an artery wall in the path the blood would follow, by deviating from the artery itinerary, because of the high curvature present at that point. The path may be found by calculating the three-dimensional direction of the vector opposite the normal vector, to the flow direction, calculated in accordance with the Frenet-Serret frame principles.

The invention claimed is:

1. A method for classifying an individual as having or not having disposition for aneurysm initiation, in a future time point, in a wall of a cerebral artery of the individual, the method comprising:
   receiving input data comprising morphological data of the cerebral artery, the morphological data comprising data indicative of at least first and second geometrical parameters comprising artery cross-sectional diameter and artery curvature of the cerebral artery at each location of predetermined locations along trajectory of the cerebral artery;
   analyzing said input data, and upon identifying at least one flow-diverting location, among said predetermined locations along the trajectory of the cerebral artery, satisfying at least two conditions comprising a first predetermined value of said artery cross-sectional diameter and a second predetermined value of said artery curvature, classifying said individual as having the disposition for aneurysm initiation, in a future time point, at said flow-diverting location of said cerebral artery, and generating classification data; and
   generating, based on the classification data, prediction data for said individual with regard to aneurysm formation in the future.

2. The method according to claim 1, wherein said analyzing of said input data comprises identification of said first predetermined value of the artery cross-sectional diameter as being a precondition for identification of said second predetermined value of the artery curvature.

3. The method according to claim 1, wherein said analyzing of said input data comprises identification of said first predetermined value of the artery cross-sectional diameter being a predetermined minimal cross-sectional diameter value, and identification of said second predetermined value of the artery curvature being a predetermined maximal curvature value which below an aneurysm will not initiate and which above an aneurysm will initiate.

4. The method according to claim 1, wherein said first and second predetermined values of respectively said artery cross-sectional diameter and artery curvature have a predetermined relation there between, being a linear function.

5. The method according to claim 1, wherein said cerebral artery comprises each dominant cerebral artery branch bifurcating at each bifurcation site along the cerebral artery, said dominant cerebral artery branch being a branch which diverts the flow of the cerebral artery.

6. The method according to claim 1, wherein said wall of said cerebral artery is at a convex side of said cerebral artery.

7. The method according to claim 1, wherein said cerebral artery is located in an intra-dural brain region.

8. The method according to claim 1, wherein said analyzing of said input data comprises applying an analysis along a centerline of said cerebral artery, to thereby identify said at least one flow-diverting location along the cerebral artery.

9. The method according to claim 1, wherein said morphological data is obtained from image data indicative of a three-dimensional image of a cerebral arterial tree.

10. The method according to claim 9, wherein said cerebral arterial tree comprises a plurality of cerebral arteries, each of said plurality of cerebral arteries starts at an entrance into intra-dural brain region or at a bifurcation site in said cerebral arterial tree.

11. A computerized system for classifying an individual as having or not having disposition for aneurysm initiation, in a future time point, in a wall of a cerebral artery of the individual, the system comprises:
   a data input utility configured and operable for receiving image data of said cerebral artery;
   a data processing utility configured and operable for:
   analyzing said image data and generating morphological data comprising artery cross-sectional diameter and artery curvature at each location of predetermined locations along trajectory of the cerebral artery, and upon identifying in said morphological data a flow-diverting location among said predetermined locations along said cerebral artery, said flow-diverting location having at least two conditions comprising a first predetermined value of said artery cross-sectional diameter and a second predetermined value of said artery curvature, classifying said individual as having the disposition for aneurysm initiation, in a future time point, at said flow-diverting location of said cerebral artery, and generating corresponding classification data; and
   an output utility configured and operable to generate output data indicative of said classification data.

12. The system according to claim 11, wherein said processing utility is configured and operable to detect whether, at each point along the cerebral artery's trajectory, the artery cross-sectional diameter value and the artery curvature value satisfy a predetermined relation there between, being a linear function.

13. The system according to claim 11, wherein said cerebral artery comprises each dominant cerebral artery branch bifurcating at each bifurcation site along the cerebral artery, said dominant cerebral artery branch being a branch which diverts the flow of the cerebral artery.

14. The system according to claim 11, wherein said wall of said cerebral artery is at a convex side of the cerebral artery.

15. The system according to claim 11, wherein said cerebral artery is located in an intra-dural brain region.

16. The system according to claim 11, wherein said identifying of said flow-diverting location comprises applying an analysis along a centerline of said cerebral artery, to thereby identify said at least one flow-diverting location along the cerebral artery.

17. The system according to claim 16, wherein said centerline comprises point centers of spheres inscribed in said cerebral artery.

18. The system according to claim 16, wherein said centerline is defined as a line with a direction defined by flow direction.

19. The system according to claim 11, wherein said image data is indicative of a cerebral arterial tree comprising a plurality of cerebral arteries, each of said plurality of cerebral arteries starts at an entrance into intra-dural brain region or at a bifurcation site in said cerebral arterial tree.

* * * * *